United States Patent
Kern et al.

(10) Patent No.: US 6,261,335 B1
(45) Date of Patent: *Jul. 17, 2001

(54) BIOSOLUBLE GLASS FIBER FILTRATION MEDIA

(75) Inventors: Charles Francis Kern, Marietta, OH (US); Michael John Cusick, Englewood, CO (US); Kenneth Andrew Clocksin, Grand Rapids; Gary Eugene Chapman, Belpre, both of OH (US)

(73) Assignee: Johns Manville International, Inc., Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/349,552

(22) Filed: Jul. 8, 1999

Related U.S. Application Data

(63) Continuation-in-part of application No. 08/827,571, filed on Mar. 28, 1997, now Pat. No. 5,945,360.

(51) Int. Cl.$^7$ .................................................. B01D 39/20
(52) U.S. Cl. ............................. 55/527; 210/505; 210/509
(58) Field of Search .............................. 55/527; 210/505, 210/509, 496; 501/35, 36, 66, 69, 72

(56) References Cited

U.S. PATENT DOCUMENTS

| | | |
|---|---|---|
| 2,692,654 * 10/1954 | Pryor | 55/527 |
| 2,823,117 * 2/1958 | Labino | 55/527 |
| 3,811,853 5/1974 | Bartholomew et al. . | |
| 3,840,359 10/1974 | Lazet . | |
| 3,972,694 * 8/1976 | Head | 210/505 |
| 4,510,252 4/1985 | Potter . | |
| 4,542,106 9/1985 | Sproull . | |
| 4,615,988 * 10/1986 | Le Moigne et al. | 501/36 |
| 5,055,428 10/1991 | Porter . | |
| 5,108,957 * 4/1992 | Cohen et al. | 501/35 |
| 5,250,488 10/1993 | Thelohan et al. . | |
| 5,332,698 * 7/1994 | Nyssen et al. | 501/35 |
| 5,332,699 * 7/1994 | Olds et al. | 501/36 |
| 5,401,693 3/1995 | Bauer et al. . | |
| 5,429,996 7/1995 | Kaneko . | |
| 5,472,467 * 12/1995 | Pfeffer | 55/527 |
| 5,583,080 12/1996 | Guldberg et al. . | |
| 5,591,453 1/1997 | Ducheyne et al. . | |
| 5,728,187 * 3/1998 | Kern et al. | 55/527 |
| 5,785,725 * 7/1998 | Cusick et al. | 210/509 |

* cited by examiner

*Primary Examiner*—Christopher Upton
(74) *Attorney, Agent, or Firm*—John D. Lister

(57) ABSTRACT

A biosoluble glass fiber filtration media includes a fibrous filtration layer of randomly oriented, entangled glass fibers which has an initial efficiency of 25% or greater as measured by ASHRAE 52.1 test method. The glass fibers forming the media have a biodissolution rate in excess of 150 ng/cm$^2$/hr and a mean diameter between about $2.5 \times 10^{-5}$ inches and about $11.0 \times 10^{-5}$ inches. Typically, the filtration layer has a thickness ranging from about 0.12 inches to about 0.35 inches and a density ranging from about 3.0 g/ft$^2$ to about 8.0 g/ft$^2$. The filtration has an initial pressure drop of about 0.35 inches of water or less and a dirt holding capacity of about 1.5 g/ft$^2$ or greater.

10 Claims, No Drawings

BIOSOLUBLE GLASS FIBER FILTRATION MEDIA

This patent application is a continuation-in-part of U.S. patent application Ser. No. 08/827,571, filed Mar. 28, 1997, now U.S. Pat. No. 5,945,360.

BACKGROUND OF THE INVENTION

The present invention relates to glass fiber filtration media and, in particular glass fiber filtration media made from glass fibers that are rapidly solubilized in biological fluids.

Glass fiber filtration media are commonly used in air filtration applications. These filtration media can be classified in two groups namely, i.e. filtration media having an average efficiency between about 25% and about 60% (low efficiency filtration media) and filtration media having an average efficiency between about 65% and about 95% (intermediate and high efficiency filtration media) based on ASHRAE—52.1 test method.

While the air filtration media currently in commercial use performs well, the manufacture and/or subsequent handling of these glass fiber filtration media may result in the formation of loose fibers which can be inhaled. As it is impractical or impossible to remove such fibers from the body, it is important to make glass fiber filtration media from glass fibers having a high degree of biosolubility, i.e. fibers which are rapidly solubilized in biological fluids, while still maintaining the physical properties and performance characteristics required of such filtration media. Since the fine diameter glass fibers (glass fibers having a mean diameter between about $2.5 \times 10^{-5}$ inches and about $12.0 \times 10^{-5}$ inches) used in these air filtration media are normally made in a flame attenuation process, preferably, a glass composition should be used to form the fibers that can be fiberized by flame attenuation processes and still be rapidly solubilized in biological fluids.

SUMMARY OF THE INVENTION

The biosoluble glass fiber filtration media of the present invention includes a fibrous filtration layer of randomly oriented, entangled glass fibers which, when made into a suitable air cleaning device, has an initial efficiency of 25% or greater as measured by ASHRAE 52.1 test method. The glass fibers forming the media have a mean diameter between about $2.5 \times 10^{-5}$ inches and about $11.0 \times 10^{-5}$ inches. Typically, the filtration layer has a thickness ranging from about 0.12 inches to about 0.35 inches and a weight ranging from about 3.0 g/ft$^2$ (grams per square foot) to about 8.0 g/ft$^2$. The filtration media has an initial flat sheet pressure drop of about 0.35 inches of water or less, with lower efficiency filtration media generally having lower initial pressure drops, and a dirt holding capacity of about 1.5 g/ft$^2$ (grams per square foot) or greater, with lower efficiency filtration media generally having the higher dirt holding capacities.

In addition to the above, the glass fibers of the filtration media of the present invention have a biodissolution rate in excess of 150 ng/cm$^2$/hr, preferably equal to or greater than 200 ng/cm$^2$/hr, more preferably equal to or greater than 300 ng/cm$^2$/hr, and most preferably equal to or greater than 400 ng/cm$^2$/hr, so that the fibers rapidly solubilize in biological fluids. Preferably, the glass fibers of the filtration media of the present invention are made from a glass composition that can be fiberized by flame attenuation processes and still retain the biodissolution rates stated above, i.e. rates in excess of 150 ng/cm$^2$/hr.

DESCRIPTION OF THE PREFERRED EMBODIMENTS

The biosoluble glass fiber filtration media of the present invention is an intermediate to high efficiency filtration media and has an average efficiency between about 65% and about 95% based on ASHRAE—52.1 test method. The filtration media includes a fibrous filtration layer of randomly oriented, entangled glass fibers which, when made into a suitable air cleaning article, has an initial efficiency of 25% or greater as measured by ASHRAE 52.1 test method and an initial flat sheet efficiency of 20% or greater as measured in a flat sheet form. The glass fibers forming the media have a mean diameter between about $2.5 \times 10^{-5}$ inches and about $11.0 \times 10^{-5}$ inches. Typically, the filtration layer has a thickness ranging from about 0.12 inches to about 0.35 inches and a weight ranging from about 3.0 g/ft$^2$ to about 8.0 g/ft$^2$. The filtration media has an initial flat sheet pressure drop of about 0.35 inches of water column or less and preferably, about 0.20 inches of water column or less. The filtration media has a dirt holding capacity of about 1.5 g/ft$^2$ or greater, preferably about 5.0 g/ft$^2$ or greater, and most preferably about 7.0 g/ft$^2$ or greater.

The fibers, once attenuated, preferably by a flame attenuation process, have a binder, such as but not limited to, a urea-phenol-formaldehyde resin applied to the fibers while the fibers are still air borne. The fibers are then collected to form an air laid mat or blanket of randomly oriented entangled fibers on a moving foraminous conveyor. The air laid mat or blanket may be formed directly on the conveyor or on an air permeable backing sheet, commonly used in the industry, such as but not limited to, a spunbond backing sheet carried on the conveyor. The air laid mat or blanket of randomly oriented, entangled glass fibers is sized in thickness, preferably without the use of mechanical devices, such as searing rolls, by applying liquid (binder and cooling water) to the fibers and to the mat while drawing air through the foraminous conveyor.

While other glass compositions may be used to form glass fibers with the required physical properties for the filtration media of the present invention, one preferred glass composition which forms glass fibers having the required physical properties, in mol percent, is as follows:

| | |
|---|---|
| SiO$_2$ | 66–69.7 |
| Al$_2$O$_3$ | 0–2.2 |
| RO | 7–18 |
| R$_2$O | 9–20 |
| B$_2$O$_3$ | 0–7.1 | where R$_2$O is an alkali metal oxide and RO is an alkaline earth metal oxide. R$_2$O is preferably Na$_2$O in most substantial part, while RO may be MgO and/or CaO, preferably both, in a molar atio of MgO/CaO of 1:3 to 3:1, more preferably 2:3 to 3:2. The chemical behavior of the glass is dictated by three ratios which the glass composition must meet, C(acid), C(bio), and C(moist). These ratios are defined compositionally as follows, all amounts being in mol percent:

$$C(acid) = [SiO_2]/([Al_2O_3] + B_2O_3] + [R_2O] + [RO])$$

$$C(bio) = ([SiO_2] + (Al_2O_3])/(B_2O_3] + [R_2O] + [RO])$$

$$C(moist) = ([SiO_2] + [Al_2O_3] + (B_2O_3])/([R_2O] + [RO]).$$

In these ratios, C(acid) is the ratio which pertains to chemical resistance in acid environments, C(bio) is the ratio which is most closely linked to biosolubility, and C(moist) is the ratio which relates to the retention of properties in moist environments. It is desired that C(acid) and C(moist) be as large as possible, while C(bio) should be as low as possible. At the same time, the HTV and liquidus of the overall composition must be suitable for glass fiber processing (preferably by a flame attenuation process). It has been found that glass fibers of high biosolubility made by flame attenuated processes maintain other necessary physical properties, such as chemical resistance and moisture resistance, when C(acid) is equal to or greater than 1.95, C(bio) is equal to or less than 2.30, and C(moist) is equal to or greater than 2.40.

Preferably, the biosoluble glass fibers used in the lightweight glass fiber insulations of the present invention, have a composition which falls within the following ranges (in mol percent):

| | |
|---|---|
| $SiO_2$ | 66–69.0 |
| $Al_2O_3$ | 0–2.2 |
| RO | 7–16 |
| $R_2O$ | 9–19 |
| $B_2O_3$ | 0–7.1 |

Most preferably, the biosoluble glass fibers used in the lightweight glass fiber insulations of the present invention, have a composition which falls within the following ranges (in mol percent):

| | |
|---|---|
| $SiO_2$ | 66–68.25 |
| $Al_2O_3$ | 0–2.2 |
| RO | 7–13 |
| $R_2O$ | 11–18 |
| $B_2O_3$ | 0–7.1 |

With respect to the performance characteristics of the glass fibers used in the filtration media of the present invention, it is preferred that C(acid) be greater than or equal to 2.00; C(bio) be less than or equal to 2.23, more preferably, less than or equal to 2.20; and that C(moist) be greater than or equal to 2.50, preferably greater than or equal to 2.60. As discussed previously, it is most desirable that C(acid) and C(moist) values be as high as possible. For example, C(moist) values of 3.00 or greater are particularly preferred. It should also be noted that the various C-ratios are independent in the sense that a more preferred glass need not have all "more preferred" C-ratios.

The acid resistance of the fibers may be measured by battery industry standard tests. For example, a typical test involves the addition of 5 grams of nominally 3 micron diameter fiber in 50 mL of sulfuric acid having a specific gravity of 1.26. Following refluxing for 3 hours, the acid phase may be separated by filtration and analyzed for dissolved metals or other elements.

The procedure used to evaluate biodissolution rate of the fibers is similar to that described in Law et al. (1990). The procedure consists essentially of leaching a 0.5 gram aliquant of the candidate fibers in a synthetic physiological fluid, known as Gamble's fluid, or synthetic extracellular fluid (SEF) at a temperature of 37° C. and rate adjusted to achieve a ratio of flow rate to fiber surface area of 0.02 cm/hr to 0.04 cm/hr for a period of up to 1,000 hours duration. Fibers are held in a thin layer between 0.2 micron polycarbonate filter media backed by plastic support mesh and the entire assembly placed within a polycarbonate sample cell through which the fluid may be percolated. Fluid pH is regulated to 7.4+0.1 through the use of positive pressure of 5% $CO_2$/95% $N_2$ throughout the flow system.

Elemental analysis using inductively coupled plasma spectroscopy (ICP) of fluid samples taken at specific time intervals are used to calculate the total mass of glass dissolved. From this data, an overall rate constant can be calculated for each fiber type from the relation:

$$k=\{d_0(1-(M/M_0)^{0.5})/2t$$

where: k is the dissolution rate constant in SEF, $d_0$ the initial fiber diameter, the initial density of the glass comprising the fiber, $M_0$ the initial mass of the fibers, M the final mass of the fibers ($M/M_0$=the mass fraction remaining), and t the time over which the data was taken. Details of the derivation of this relation is given in Leinweber (1982) and Potter and Mattson (1991). Values for k may be reported in $ng/cm^2/hr$ and preferably exceed a value of 150. Replicate runs on several fibers in a given sample set show that k values are consistent to within 3 percent for a given composition.

Data obtained from the above outlined evaluation can be effectively correlated within the sample set chosen-dissolution data used to derive k's were obtained only from experimental samples of uniform 3.0 micron diameter and under identical conditions on initial sample surface area per volume of fluid per unit time, and sample permeability. Data was obtained from runs of up to days to obtain an accurate representation of the long term dissolution of the fibers. From these evaluations, the preferred biodissolution rate constants k (in $ng/cm^2/hr$) for glass fibers used in the lightweight glass fiber insulations of the present invention are greater than 150 $ng/cm^2/hr$, preferably equal to or greater than 200 $ng/cm^2/hr$, more preferably equal to or greater than 300 $ng/cm^2/hr$, and most preferably equal to or greater than 400 $ng/cm^2/hr$.

To the determine moisture resistance of the glass fibers, a stress corrosion test is used in which fibers are stressed by bending the fibers in a controlled humidity and temperature test chamber. Fibers which exhibit moisture resistance under these conditions take longer to break.

With respect to the preferred glass compositions used to form the glass fibers used in the filtration media of the present invention, by the term "consisting essentially of" is meant that additional ingredients may be added to the composition provided the additional ingredients do not substantially alter the nature of the composition. Substances which cause the biodissolution rate of fibers made from the glass composition to drop below 150 $ng/cm^2/hr$ or which make the composition unsuitable for forming fibers having a mean of diameter between about 2.5 microns and about 11.0 microns and a biodissolution rate in excess of 150 $ng/cm^2/hr$ by a flame attenuation process are substances which do substantially alter the composition. As used herein the term "a flame attenuation process" refers to a fiberization process wherein the final attenuation step of the process involves the introduction of the glass fibers directly into a hot, high velocity burner flame. In many processes, typically rotary fiberization processes, the final attenuation step of the process involves the introduction of the glass fibers into high velocity streams of heated air and combustion gases which are relatively cool when compared to the temperatures of the flames used in the flame attenuation processes. When used in flame attenuation processes, glass compositions used in other than flame attenuation processes to form fibers having biodissolution rates in excess of 150 $ng/cm^2/hr$, in general, do not form fibers having biodissolution rates in excess of 150 $ng/cm^2/hr$. Since the preferred method of forming the glass fibers used in the preferred filtration media of the present invention is by means of a flame attenuation process, glass compositions which can form fibers of the required diameter with the required biodissolution rate of 150 ng/cm²/hr in a flame attenuation process are preferred. While the reverse is not generally true, the preferred glass compositions of the present invention, which can form fibers of the required diameter with the required biodissolution rate in excess of 150 ng/cm²/hr in a flame attenuation process, can be used to form fibers with the required biodissolution rate in the rotary fiberization processes mentioned above. Preferably, the glass compositions are free of iron oxides, lead oxides, fluorine, phosphates ($P_2O_5$), zirconia, and other expensive oxides, except as unavoidable impurities.

The following table shows the flat sheet tested physical properties of filtration media of the present invention (Media A–D) relative to the tested physical properties of comparable commercial ASHRAE filtration media (Media AA–DD) with the comparable filtration media being in the same column.

| Physical Properties | Media A | Media B | Media C | Media D |
|---|---|---|---|---|
| Thickness (inches) | 0.29 | 0.25 | 0.28 | 0.23 |
| Density (% of nominal) | 105 | 101 | 104 | 97 |
| Binder (% by weight) | 14.3 | 13.5 | 15.8 | 16.6 |
| Initial Flat Sheet Pressure Drop (inches of water col.) | 0.17 | 0.28 | 0.22 | 0.40 |
| Initial Flat Sheet Efficiency | 53.8% | 74.2% | 66.0% | 83.0% |
| Dirt Loading | 29.5 | 10.8 | 23.3 | 5.8 |
| Air Erosion | Pass | Pass | Pass | Pass |

| | Media AA | Media BB | Media CC | Media DD |
|---|---|---|---|---|
| Thickness (inches) | 0.30 | 0.25 | 0.30 | 0.28 |
| Density (% of nominal) | 104 | 102 | 103 | 99 |
| Binder (% by weight) | 14.3 | 14.2 | 13.8 | 13.5 |
| Initial Flat Sheet Pressure Drop (inches of water col.) | 0.17 | 0.28 | 0.22 | 0.35 |
| Initial Flat Sheet Efficiency | 53.8% | 74.1% | 63.4% | 79.4% |
| Dirt Loading | 27.6 | 7.9 | 24.4 | 11.2 |
| Air Erosion | Pass | Pass | Pass | Pass |

As shown in the above table, the physical properties for the biosoluble filtration media of the present invention are comparable to the physical properties of current commercial filtration media while providing a product that is rapidly solubilized in biological fluids. While the initial pressure drop for filtration media D was greater than the initial pressure drop for comparable filtration media DD, the higher initial pressure drop may have been due to its higher filtration efficiency which was also greater than the filtration efficiency of filtration media DD.

The efficiency ratings given to the filtration media of the of the present invention are based on the following testing procedure. An air stream, with 0.3 to 0.5 micron mineral oil droplets, is passed through a two foot square section of the filtration media at a velocity of twenty-five feet per minute. The number of droplets in the air stream, upstream of the filtration media, is compared to the number of droplets in the air stream, downstream of the filtration media, to determine the efficiency. The initial efficiency rating for the filtration media is the efficiency measured at the beginning of the test run with no dust or dirt loading.

During the testing procedure, dust particles are added to the filtration media section by passing an air stream containing the dust particles through the filtration media section at a velocity of twenty-five feet per minute. When the pressure drop across the filtration media reaches one inch of water column, the filtration media is considered plugged and the test is completed. The average air filtration efficiency rating for the filtration media is an average of the measured air filtration efficiencies of the filtration media as measured when the pressure drop across the fibrous filtration layer reaches certain levels during the test. The efficiency measurements made to determine the average air filtration efficiency of the filtration media are made: at the beginning of the test, at the end of the test (when the pressure drop across the filtration media is one inch of water column), and when the dust loading of the filtration media causes the pressure drops, across the filtration media, to be at the following levels: 25%, 50% and 75% of the way between the initial pressure drop across the filtration media and the final pressure drop across the filtration media of one inch of water column.

The above discussed efficiency measurements are based on the mechanical trapping of dust particles by the filtration media and are not based on efficiencies which can be obtained, with certain filtration media, by means of an electrostatic charge on the fibers of the filtration media attracting and capturing charged dust particles present in an air or gas stream or by applying tackifiers, such as oils, to the fibers of the blanket to which dust particles in the air or gas stream adhere.

The "dust or dirt-holding capacity" of the filtration media is the weight of dust particles, in grams, that causes the two foot square section of the filtration media being tested to have a one inch of water column pressure drop across its thickness.

The thicknesses of the filtration media set forth in this specification are measured by placing a one foot square 630 gram weight on a one foot square section of the filtration media and measuring the thickness of the filtration media when compressed by the weight.

In describing the invention, certain embodiments have been used to illustrate the invention and the practices thereof. However, the invention is not limited to these specific embodiments as other embodiments and modifications within the spirit of the invention will readily occur to those skilled in the art on reading this specification. Thus, the invention is not intended to be limited to the specific embodiments disclosed, but is to be limited only by the claims appended hereto.

What is claimed is:

1. A biosoluble glass fiber filtration media, comprising:
   a fibrous filtration layer of randomly oriented, entangled flame attenuated glass fibers; the glass fibers being prepared from a glass composition consisting essentially of, in mol percent:

| | |
|---|---|
| $SiO_2$ | 66–69.7 |
| $Al_2O_3$ | 0–2.2 |
| RO | 7–18 |
| $R_2O$ | 9–20 |
| $B_2O_3$ | 0–7.1 | the glass composition having a C(acid) $\geq 1.95$, a C(bio) $\leq 2.30$, and a C(moist) k $\geq 2.40$; the glass fibers having a biodissolution rate in excess of 150 ng/cm²/hr; the glass fibers have a mean diameter between about $2.5 \times 10^{-5}$ inches and about $11.0 \times 10^{-5}$ inches; and
   the fibrous filtration media having an average efficiency of 65% or greater as measured by ASHRAE 52.1 test method; the filtration layer having a thickness ranging from about 0.12 inches to about 0.35 inches; the filtration layer having a weight ranging from about 3.0 g/ft$^2$ to about 8.0 g/ft$^2$; the filtration having an initial flat sheet pressure drop of 0.35 inches of water or less; and a dirt holding capacity of about 1.5 g/ft$^2$ or greater.

2. The biosoluble glass fiber filtration media according to claim 1, wherein:

the glass fibers have a biodissolution rate in excess of 300 ng/cm$^2$/hr.

3. The biosoluble glass fiber filtration media according to claim 1, wherein:

the glass fibers have a biodissolution rate in excess of 400 ng/cm$^2$/hr.

4. The biosoluble glass fiber filtration media according to claim 3, wherein:

the glass fibers are bonded together at their points of intersection by a binder.

5. The biosoluble glass fiber filtration media according to claim 1, wherein:

the glass fibers are prepared from a glass composition consisting essentially of, in mol percent:

| | |
|---|---|
| SiO$_2$ | 66–69.0 |
| Al$_2$O$_3$ | 0–2.2 |
| RO | 7–16 |
| R$_2$O | 9–19 |
| B$_2$O$_3$ | 0–7.1 |

6. The biosoluble glass fiber filtration media according to claim 5, wherein:

the glass fibers have a biodissolution rate in excess of 300 ng/cm$^2$/hr.

7. The biosoluble glass fiber filtration media according to claim 5, wherein:

the glass fibers have a biodissolution rate in excess of 400 ng/cm$^2$/hr.

8. The biosoluble glass fiber filtration media according to claim 1, wherein:

the glass fibers are prepared from a glass composition consisting essentially of, in mol percent:

| | |
|---|---|
| SiO$_2$ | 66–68.25 |
| Al$_2$O$_3$ | 0–2.2 |
| RO | 7–13 |
| R$_2$O | 11–18 |
| B$_2$O$_3$ | 0–7.1. |

9. The biosoluble glass fiber filtration media according to claim 8, wherein:

the glass fibers have a biodissolution rate in excess of 300 ng/cm$^2$/hr.

10. The biosoluble glass fiber filtration media according to claim 8, wherein:

the glass fibers have a biodissolution rate ih excess of 400 ng/cm$^2$/hr.

* * * * *